United States Patent [19]
Lui

[11] Patent Number: 5,304,155
[45] Date of Patent: Apr. 19, 1994

[54] VALVED CATHETER

[75] Inventor: Chun K. Lui, Monroeville, Pa.

[73] Assignee: Cook Pacemaker Corporation, Leechburg, Pa.

[21] Appl. No.: 87,644

[22] Filed: Jul. 12, 1993

Related U.S. Application Data

[63] Continuation-in-part of Ser. No. 913,243, Jul. 14, 1992, Pat. No. 5,261,885.

[51] Int. Cl.$^5$ .................. A61M 1/00; A61M 5/00; F16K 15/14
[52] U.S. Cl. .................. 604/247; 604/31; 137/849
[58] Field of Search .................. 604/30, 31, 52, 53, 604/93, 245–247, 256; 137/844, 845, 849

[56] References Cited

U.S. PATENT DOCUMENTS

| | | | |
|---|---|---|---|
| 3,734,126 | 5/1973 | Weaver | 137/512.15 |
| 3,888,249 | 6/1975 | Spencer | 604/247 |
| 3,995,617 | 12/1976 | Watkins et al. | 604/247 X |
| 4,759,752 | 7/1988 | Stöber | 604/247 |
| 5,112,301 | 5/1992 | Fenton, Jr. et al. | 604/30 |
| 5,160,325 | 11/1992 | Nichols et al. | 604/247 |
| 5,180,364 | 1/1993 | Ginsburg | 604/53 |
| 5,224,938 | 7/1993 | Fenton, Jr. | 604/247 |

FOREIGN PATENT DOCUMENTS

8002230 10/1980 World Int. Prop. O. .......... 604/247

Primary Examiner—John D. Yasko
Assistant Examiner—Adam J. Cermak
Attorney, Agent, or Firm—Richard J. Godlewski

[57] ABSTRACT

A closed-end catheter having a flat-surfaced valve positioned in a recess about the distal portion of the catheter for preventing retrograde flow of blood therethrough when positioned in a blood vessel of a patient. The valve catheter comprises a flexible material, cylindrical tube having a semi-circular cross-sectional wall extending longitudinally about the distal portion thereof. The laterally facing valve is formed in a planar surface of a flexible material layer attached to the wall in the distal portion of the cylindrical tube. One or more passages extend through the cylindrical tube in which medicaments or fluids can be simultaneously injected or aspirated. The valve is formed by inserting one or more flat-surfaced rods in the passages of the tube to stretch the surrounding wall. A flat-surfaced layer of flexible material is applied over the flat-surfaced rod to the stretched wall. The flexible material layer is cured and one or more longitudinally offset apertures are formed therein with the rods remaining in the passages of the tube. The rods are then removed and a plug inserted into the passages to close the distal end of the catheter. The stretched wall of the distal portion compresses the fluid apertures to a closed position to prevent fluid leakage therethrough when in a relaxed condition.

26 Claims, 4 Drawing Sheets

VALVED CATHETER

CROSS-REFERENCE TO RELATED APPLICATIONS

This application is a continuation-in-part of application Ser. No. 07/913,243, filed Jul. 14, 1992, now U.S. Pat. No. 5,261,885, and entitled "A Valved Catheter".

TECHNICAL FIELD

This invention relates generally to medical devices such as catheters and, in particular, to catheters with fluid valves.

BACKGROUND OF THE INVENTION

Catheters are often positioned in the vascular system of a patient for long-term drug infusion or fluid aspiration. A problem with leaving a catheter positioned in the vascular system of a patient for a long duration is that thrombosis occurs at the distal end of the catheter lumen where there is even a small amount of retrograde blood flow into the catheter. In the vascular system, blood clots form quickly and thrombosis obstructs a catheter lumen over time. A thrombotic obstruction makes the catheter lumen useless and creates a risk for the patient. If a catheter lumen is only partially obstructed by thrombosis and fluid is injected therethrough, a thrombus is flushed loose from the catheter lumen and flows through the vascular system to a narrow diameter site. As a result, the loose thrombus potentially causes an undesirable obstruction in a small or narrowed vessel of the vascular system. If the thrombus obstructs a small vessel in the lung, heart, or brain, serious complications such as pulmonary embolism, heart attack, or stroke may result.

One approach to preventing retrograde fluid flow into a catheter lumen is the use of a catheter having sufficient rigidity for introduction into tissue to provide epidural anesthesia. The rigid catheter includes several longitudinal slits in the catheter wall about the distal end thereof. A limitation of this rigid catheter is that it is not flexible or pliable for atraumatic introduction through the tortuous vessels of the vascular system.

Another approach to preventing the retrograde blood flow that causes thrombosis is the use of a closed end, silicone catheter with a single, linearly extending, two-way slit valve near the distal end thereof. The slit valve is contiguous with the silicone rubber catheter wall, which is treated with dimethylsiloxane for weakening the wall adjacent the valve. A problem with the use of this slit valve is that the valve is positioned on the circumference of the catheter wall. The sides of the slit valve are inadequately supported by the adjacent, curved catheter wall. The inadequately supported sides of the slit valve fail to form a watertight seal and, as a result, permit leakage. Another problem with the use of this slit valved catheter is that the catheter wall adjacent the valve is weakened by dimethylsiloxane, which further decreases support for the slit valve. As a result, the valve is susceptible to improper or crooked closure and retrograde blood leakage. Furthermore, the weakened catheter wall makes the slit valve more fragile and susceptible to damage in repeated operation. In addition, the weakened wall potentially causes collapse of the slit valve against the opposite inner wall of the catheter, thereby preventing use of the valve for aspiration.

Yet another problem with the use of this silicone, slit valved catheter is that the catheter has a smooth exterior surface without a traverse protrusion. As a result, the slit valve is positioned on the circumferential periphery of the catheter adjacent or possibly abutting a blood vessel wall. During irrigation, fluid flow is flushed out of the slit valve and directly against the intimal layer of the blood vessel wall. This fluid flow deflects off the blood vessel wall and creates turbulence in the blood vessel lumen, thereby loosening particles of plaque and other deposits from the blood vessel wall. The loosened particles flow through the vascular system and present the risk of obstructing a small or partially occluded blood vessel. As previously discussed, undesirable obstructions can cause pulmonary embolism, heart attack, or stroke in a patient. During aspiration, the blood vessel wall is potentially drawn against and possibly into the slit valve. As a result, the blood vessel wall can be traumatized and damaged, which causes thrombosis and other cell proliferation and deposition to occur and subsequently obstruct the catheter or blood vessel. Again, trauma to the blood vessel wall loosens plaque and other deposits therefrom and presents the risk of undesirable obstructions as previously discussed.

Yet another problem with this catheter is that the size of the catheter and the durometer of the catheter material must be designed to meet the needs of a particular valve design. This significantly limits the inside and outside diameters of the catheter along with the wall thickness. The durometer of the catheter material can be utilized to change the dimensions of the catheter to meet a particular valve design; however, the range of catheter dimensions and material durometer is still limited.

SUMMARY OF THE INVENTION

The foregoing problems are solved and a technical advance is achieved in an illustrative closed-end catheter having a valve positioned in a recess about the distal portion of the catheter. The valve includes a fluid aperture that communicates with the exterior of the catheter and a longitudinal passage within the catheter. The outer wall of the catheter about the distal portion thereof advantageously compresses the fluid aperture to a closed position for preventing retrograde blood flow and thrombosis about the distal end of the catheter when positioned in a blood vessel of a patient.

The valved catheter comprises an elongated member such as a flexible material, cylindrical tube having a distal portion, an outer wall, and a passage extending longitudinally therein. The recess is formed in the outer wall extending longitudinally along the distal portion of the elongated member. The valve is positioned in the recess of the elongated member and attached to the outer wall about the distal portion. The flat-surfaced valve is formed by positioning in the passage along the distal portion a rod having a flat surface extending longitudinally therealong. The rod laterally stretches the outer wall along the distal portion. To form the valve, a flat-surfaced layer of flexible material is attached over the flat-surfaced rod to the stretched outer wall along the distal portion. The fluid aperture is formed by placing a longitudinal slit in the layer of flexible material with the rod in the passage. The rod is subsequently removed, and a plug is inserted in the passage to close the distal end of the catheter. The laterally stretched outer wall along the distal portion now advantageously compresses the fluid aperture to a predetermined closed position for preventing fluid leakage therethrough.

The fluid aperture comprises a longitudinal slit formed through the flat-surfaced layer of flexible material that communicates exterior to and with the passage of the elongated member.

The distal portion of the outer wall is substantially U-shaped and compresses the slit to the closed position for advantageously preventing fluid flow therethrough. The flat-surfaced layer of the flexible material is longitudinally attached to the U-shaped outer wall. The closed distal end of the catheter includes a plug that is positioned in and closes the distal end of the passage of the elongated member tube.

The valved catheter of the present invention can also be considered as comprising an elongated tubular member with a longitudinal passage extending therethrough to a lateral facing valve in the region of the distal end of the catheter. The valved catheter is characterized in that the tubular member in the region of the distal end is of reduced cross-section and has a planar surface. The valved catheter is also characterized in that a valve is formed in the planar surface. In one aspect, the outer wall of the elongated tubular member can form the planar surface.

In the formation of the valved catheter of the present invention, a longitudinally extending section of the tubular member has been removed in the region of the distal end and material has been attached to the member in the region to form a planar surface. The material is fixed to the member in the region of the distal end while the latter is in a pre-stressed condition. The pre-stressed condition advantageously serves to ensure that the valve is in a normally closed condition. The member in the region of the distal end is substantially U-shaped, and the material is flexible and extends across the ends in the member of the region of the distal end.

The valved catheter of the present invention also advantageously includes a second valve formed in the planar surface for simultaneous delivery of incompatible medicants or the simultaneous injection and aspiration of fluids. The valved catheter also includes a second longitudinal passage extending through the tubular member which is in sole communication with the second valve. Each valve is in the form of a slit extending through the planar surface, and the outer surface of the tubular member in the region of the distal end has a semi-circular cross-sectional shape. As a result, the tubular member in the distal portion or about the distal end thereof is pre-stressed to urge the slits to a closed condition. The flexible material is attached over the first and second passages, and the slits are longitudinally offset along the passages. Advantageously, each slit does not interfere with the operation of the other valve. Each of the passages is closed at the distal end thereof by a plug. The passages in the region of the distal end of the member are formed by temporarily positioning a flat-surfaced rod in each passage during the formation of the catheter.

The foregoing problems are also solved and a technical advance is achieved in an illustrative closed-end catheter having a valve in a planar surface about the distal portion of the catheter. The catheter includes an elongated tubular member with first and second passages extending longitudinally therein with a reduced cross section and a planar surface in the distal portion thereof. The valve includes first and second fluid apertures that communicate with the exterior of the catheter and the longitudinal passages within the catheter. The wall of the elongated tubular member advantageously compresses the fluid apertures to a closed position for preventing retrograde blood flow and thrombosis about the distal end of the catheter when positioned in the vessel of a patient.

The reduced cross section and planar surface in the distal portion of the elongated tubular member is formed in the wall thereof by removing or cutting away a portion of the tubular member through the first and second passages. The planar surface is formed by a flat surface layer of flexible material attached to the wall in the distal portion of the tubular member. The fluid apertures are slits formed through the flat surfaced layer of the flexible material that communicate exterior to the passages of the tubular member. The outer surface of the wall along the distal portion has a substantially semi-circular cross-sectional shape that compresses the slits to a closed position. To form the valve, flat surface rods are positioned in the passages of the tubular member about the distal portion. A flat surfaced layer of flexible material is attached over the rods and to the stretched wall along the distal portion. The flexible material is attached to the wall of the elongated member with the rods in their respective passages. The fluid apertures are formed by placing longitudinally offset slits in the layer of the flexible material with the rods in the passages. The rods are subsequently removed and plugs positioned in the distal ends of the passages to close the distal end of the catheter. In addition, laterally extending portions are formed in the rods extending from the flat surface in each rod to relieve stretching of the wall adjacent a wide segment of the flat surface of the adjacent rod where the fluid apertures are formed therein. Advantageously, this minimizes, if not eliminates, interaction between the valves during operation thereof. Furthermore, only the wall adjacent the desired slit is stretched to put the slit in a pre-stressed condition.

DETAILED DESCRIPTION

Figure 1:
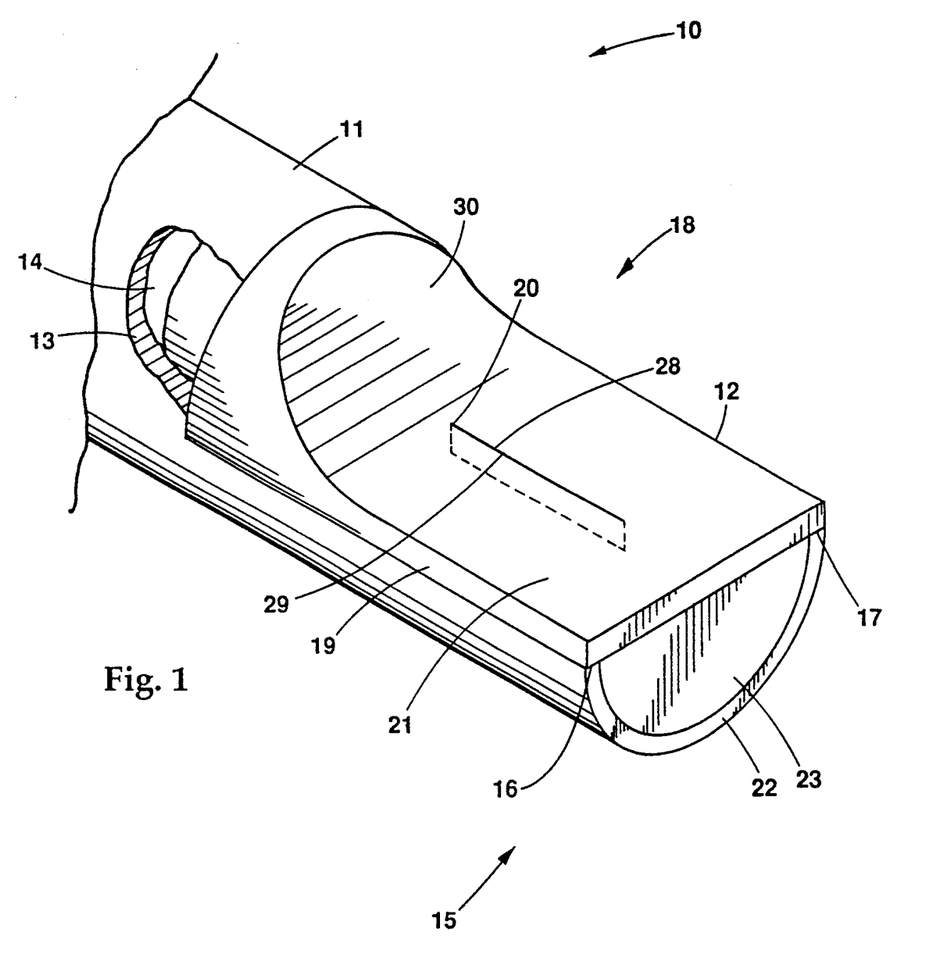
FIG. 1 depicts a pictorial view of a distal end segment of an illustrative valved catheter of the present invention.

Depicted in FIG. is a pictorial view of the distal end segment of illustrative valved catheter 10 comprising elongated tubular member 11 and laterally facing valve 12 with compressed, closed fluid aperture 20 positioned about or in the region of the distal end of the catheter. The proximal end (not shown) of the valved catheter is connected, for example, to a commercially available implantable port or a connector fitting for the injection or aspiration of fluids such as medicaments, blood, and the like. When the valved catheter is positioned in a blood vessel of a patient, the fluid aperture prevents retrograde blood flow and thrombosis about the distal end of the catheter. The valved catheter further comprises closed distal end 22 formed by plug 23 positioned in passage 14 of member 11 for preventing longitudinal fluid flow from the catheter.

Elongated tubular member or tube 11 includes outer wall 13 and passage 14 extending longitudinally therethrough. Elongated tubular member 11 further includes longitudinal recess 18 for forming U-shaped distal portion 15 with ends 16 and 17 positioned at the top of the two sides of the U-shaped portion. Recess 18 and U-shaped distal portion 15 provide for the attachment of valve 12 to the elongated member tube. Recess 18 is formed by removing a longitudinally extending section of the tubular member in the region of the distal end. As a result, the tubular member has a reduced cross section in the distal portion or in the region of the distal end. The tubular member can be integrally formed with a planar surface or a flat-surfaced layer of flexible material can be attached to U-shaped distal portion 15.

Elongated tubular member 11 is a flexible material cylindrical tube comprising, for example, commercially available 1.6 mm silicone material tube with an outside diameter of approximately 0.125", an inside diameter of approximately 0.062", and a length of approximately 70 cm. The silicone material of elongated member tube 11 has a durometer of approximately 65 on the Shore A scale. Recess 18 is, for example, approximately 0.061±0.002" in height and 0.515±0.017" in length extending proximally from the distal end of the elongated member tube.

Valve 12 comprises slit or fluid aperture 20 formed in flat surface 21 of flexible material layer 19. The fluid aperture provides for the flow of fluid between passage 14 and the exterior of the valved catheter. Flat surface 21 of the flexible material layer provides for both sides of the fluid aperture to present squarely abutting surfaces 28 and 2 when valved catheter 10 is at rest and the fluid aperture is compressed closed. Flexible material layer 19 is attached to outer wall 13 of the elongated member longitudinally along ends 16 and 17 of the U-shaped distal portion. The width of the flexible material layer (0.130") is greater than the outside diameter (0.125") of the distal portion of the elongated member where the flexible material layer is attached at ends 16 and 17. The flexible material layer is fixed to the member in the region of the distal end, while the latter is in a pre-stressed condition. This serves to ensure that the valve is in a normally closed condition or position. When the valved catheter is at rest, the U-shaped ends 16 and 17 of the elongated member tube compress the flexible material layer for forcing the slit or fluid aperture to a closed position, thereby preventing fluid leakage or retrograde blood flow. When the valved catheter is in use, the force of fluid being injected or withdrawn through passage 14 causes abutting slit surfaces 28 and 29 to laterally stretch, thereby permitting flow through fluid aperture 20.

Flexible material layer 19 comprises a material with a desirable durometer and a curing mechanism that is similar to that of the silicone tubing material of elongated member 11. Flexible material layer 19 preferably comprises, for example, a silicone material such as Silastic Q7-4850 commercially available from Dow Corning, Midland, Mich. This Silastic Q7-4850 material has a durometer of approximately 50 on the Shore A scale. Flexible material layer 19 is, for example, approximately 0.015±0.000" and −0.005" thick, 0.500±0.015" long, and 0.130" wide, with a radius of approximately 0.050±0.010" at proximal, upper curved portion 30 thereof for providing flat surface area 21, which extends from the curved portion to the distal end of the elongated member tube. Although the radius in the flexible material layer does not affect valve function, sharp corners on the catheter are preferably avoided and rounded off as needed for facilitating atraumatic introduction of the valved catheter into the vessels of the vascular system of a patient. Fluid aperture 20 is, for example, a slit approximately 0.236±0.015" in length and extends longitudinally along the flat surface area of the flexible material layer beginning 0.157±0.015" from the proximal end of the flexible material layer. Plug 23 comprises, for example, the same material as the flexible material layer, which is classified as a liquid silicone and is injected into the passage of the elongated member tube and then heated and cured for forming the closed distal end of the elongated member tube.

Ten valved catheters identical to the above-described valved catheter 10 were immersed in a 37° C. solution having the same viscosity of blood for simulating in vivo conditions. A Vital-Port ® reservoir, commercially available from Cook Pacemaker Corporation, Leechburg, Pa., was attached to each catheter. A 20 gauge needle with syringe was inserted in the port septum for repeated cycles of injection and withdrawal through the valved catheter. The syringe was driven by an air cylinder which was set to inject and withdraw 10 cc for each stroke of the syringe. The duration of each cycle was 30 seconds. Each of the tested valved catheters underwent 2500 cycles of injection/withdrawal. The valve-opening pressures for injection and withdrawal were measured at the beginning of the test and every 500 cycles thereafter.

Pressures recorded prior to testing and at 500 cycle intervals through 2500 cycles exhibited average injection pressures ranging from 0.3 to 0.7 psi. Average withdrawal pressures recorded at the same intervals ranged from 2.3 to 3.2 psi. Visual inspection of the catheter valves showed no damage through the test, indicating valve integrity was maintained. Throughout testing, positive and negative pressures were required to open the valve for injection and withdrawal, respectively, indicating the valve functioned properly by remaining closed unless subjected to a differential pressure.

Alternatively, the compression force imposed on the fluid aperture is varied by using different materials for the flexible material layer or elongated member tube or by modifying the durometer of the materials used, the dimensions of the flexible material layer, or the relative inner and outer diameters of the elongated member tube and distal portion thereof. However, a valve can be attached to virtually any size and durometer elongated member tube.

Figure 2:
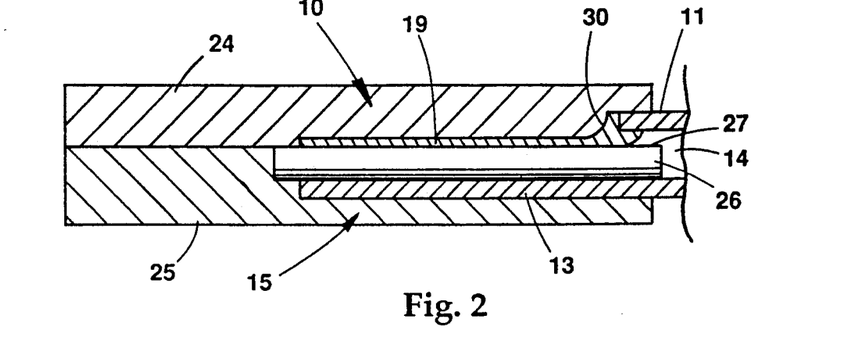
FIGS. 2–4 depict an illustrative method of forming the valved catheter of FIG. 1.
Figure 3:
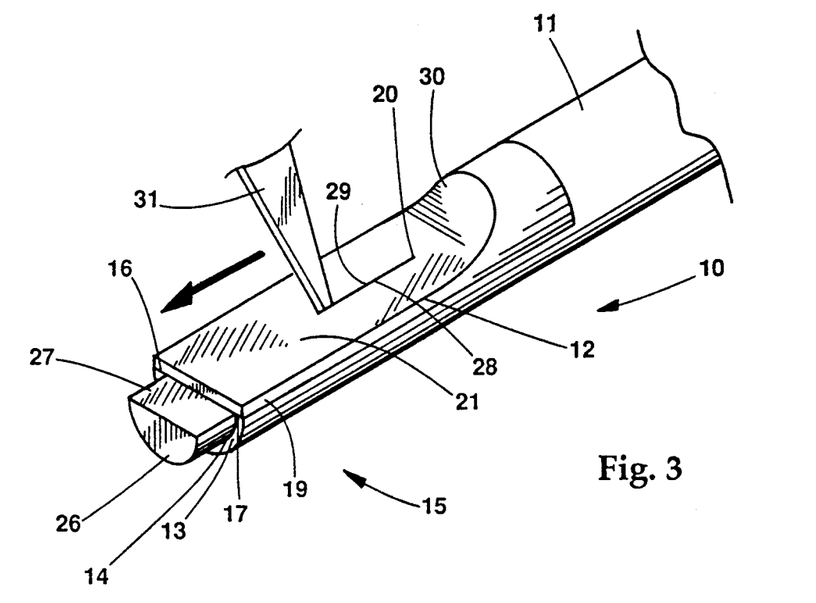
Figure 4:
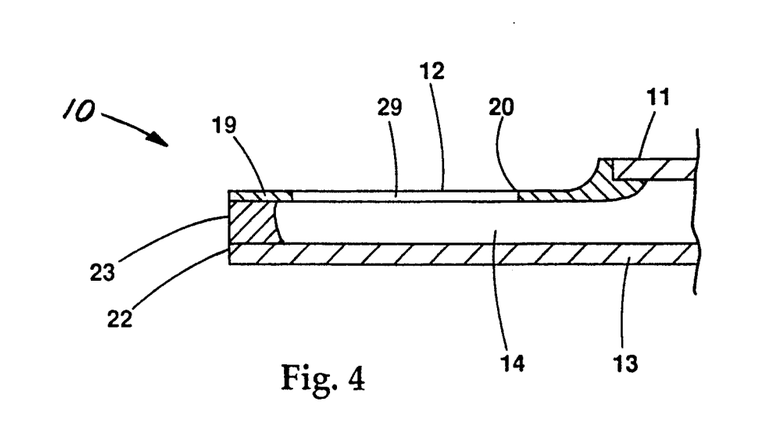

A preferred method of forming illustrative valved catheter 10 is depicted in FIGS. 2–4. FIG. 2 depicts a cross-sectioned longitudinal view of elongated member tube 11 positioned between well-known mold halves 24 and 25 with flat-surfaced pin or rod 26 positioned in passage 14 of the elongated member tube. Rod 26 is a round, metal hardened pin such as a gauge pin or drill blank that has been ground down for forming flat surface 27 (shown in FIG. 3) extending longitudinally therealong. Rod 26 has, for example, a maximum outside diameter of 0.067" and a cross-sectional height of 0.033". Elongated member tube 11 has been cut longitudinally in outer wall 13 to form recessed, U-shaped distal portion 15 and has a reduced cross section in the distal portion or in the region of the distal end. Since elongated member tube 11 has a passage with an inside diameter of 0.062", rod 26 positioned in the passage laterally stretches the outer wall of the elongated member tube to an inside diameter of 0.067" and an outside diameter of 0.130". Flexible material layer 19 is applied over the flat surface of the rod and over the laterally stretched, U-shaped outer wall of distal portion 15 of the elongated member. The elongated member tube with flexible material layer positioned over the laterally stretched distal portion thereof and the rod positioned in the passage are heated for fixedly attaching the flexible material layer to the elongated member tube and curing the materials.

FIG. 3 depicts a pictorial view of elongated member tube 11 and flexible material layer 19 fixedly attached with rod 26 positioned in passage 14 and removed from the mold halves shown in FIG. 2. Flat surface 21 of the flexible material layer is cut longitudinally using knife 31 to form slit or fluid aperture 20. When the slit is being cut, rod 26 with flat surface 27 remains in passage 14 for laterally stretching ends 16 and 17 of outer wall 13 about distal U-shaped portion 15.

FIG. 4 depicts a cross-sectioned longitudinal view of the valved catheter with the rod removed from passage 14 and a plug 23 positioned at distal end 22 of the elongated member tube for providing a closed distal end. The plug is affixed to elongated member tube 11 and flexible material layer 19 by injecting material into the distal end of passage 14 and then heating and curing the material. When the rod is removed from the passage of the elongated member, the U-shaped ends of outer wall 13 want to return to an inside diameter of 0.062" and an outside diameter of 0.125" and, as a result, compress flexible material layer 19 and forcibly close fluid aperture 20.

Figures 5, 6:
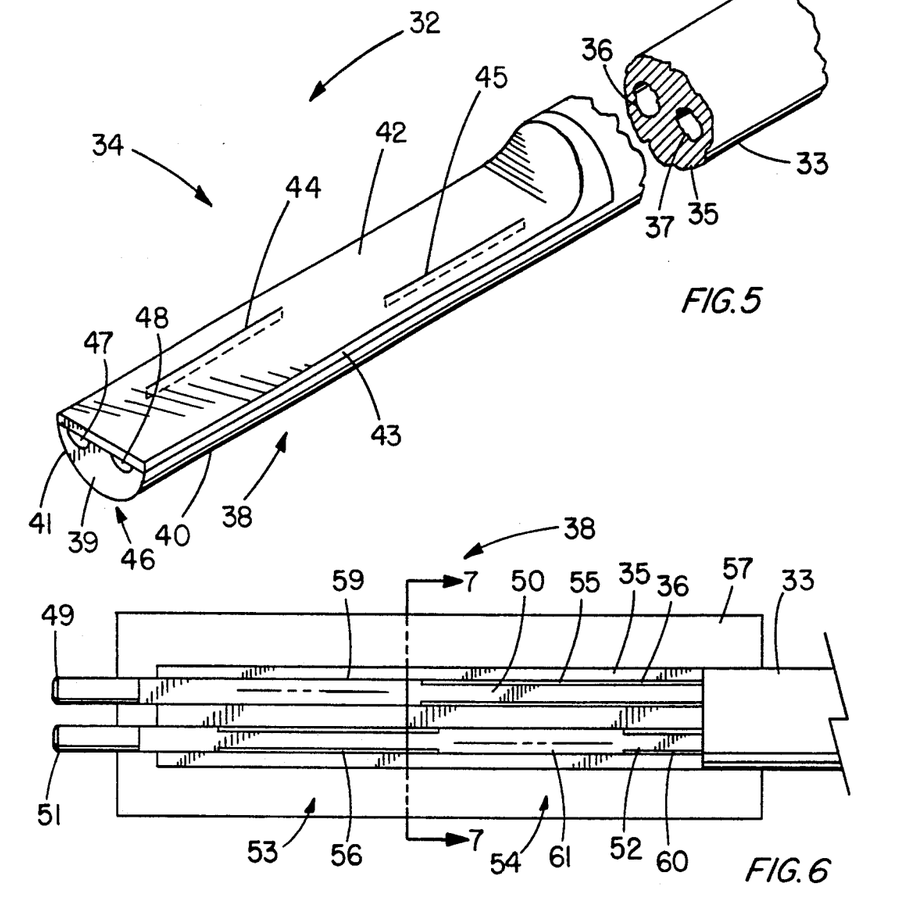
FIG. 5 depicts a pictorial view of another embodiment of an illustrative valved catheter of the present invention with dual passages therein.
FIGS. 6–9 depict an illustrative method of forming the valved catheter of FIG. 5.

FIG. 5 depicts a pictorial view of another illustrative embodiment of valved catheter 32 comprising elongated tubular member 33 and laterally facing valve 34 in planar surface 42 in distal portion 38 of or in the region of the distal end of the elongated member. The elongated member has first and second adjacent passages 36 and 37 extending longitudinally therethrough and a reduced cross section 39 and planar surface 42 in distal portion 38. The valve has first and second fluid apertures 44 and 45 communicating exterior to and with the first and second adjacent passages of the elongated member, respectively. This valved catheter with multiple, and, in particular, dual passages or lumens advantageously provides for the injection of incompatible medicaments in an area of the vascular system that is highly turbulent for mixing and dispersing the medicaments without causing undue trauma to one or more vessels of the vascular system. In addition, this dual passage, valved catheter provides for simultaneous injection and aspiration of the vascular system. The fluid apertures of the valved catheter prevent retrograde blood flow and thrombosis about the distal end of the catheter. Distal end 46 of the valved catheter is closed by plugs 47 and 48 inserted in first and second passages 36 and 37, respectively. The closed distal end prevents longitudinal fluid flow from the valved catheter.

Elongated tubular member 33 is a cylindrically shaped tube including wall 35 and first and second passages 36 and 37 extending longitudinally therethrough. In the region proximate distal end 46 of the elongated tubular member, a segment of the tubular member is removed or cut away to form distal portion 38 which has a reduced cross section 39 as compared to the cylindrical cross section of the remaining portion of the tubular member. Approximately half of the tubular member is longitudinally removed in the region of the distal end to form a reduced cross section wherein outer surface 40 of the wall along the distal portion has a substantially semi-circular cross-sectional shape 41. Planar surface 42 comprises a flat-surface layer 43 of flexible material attached to the wall in the distal portion. Longitudinally offset fluid tight apertures 44 and 45 are formed through the planar surface and communicate exterior to and with first and second passages 36 and 37, respectively.

Elongated tubular member 33 is a flexible material cylindrical tube comprising, for example, commercially available silicone material tubing with an outside diameter of 0.150" and inside diameters of approximately 0.047" for first and second passages 36 and 37 and a length of approximately 70 cm. The silicone material of elongated tubular member 32 has a durometer of approximately 65 on the Shore A scale. Reduced cross section 39 has a height of approximately 0.074". The length of distal portion 38 is approximately 0.857" extending proximally from the distal end of the elongated tubular member.

Valve 34 is positioned through planar surface 42, which comprises a flat-surface layer 43 of material attached to wall 35 and over first and second passages 36 and 37. The thickness of the flexible material layer is approximately 0.010". First aperture or slit 44 is approximately 0.236" in length and starts approximately 0.110" from distal end 46 of the catheter. Second aperture or slit 45 is also approximately 0.236" in length and approximately 0.446" from distal end 46. The planar surface of the flat-surface layer of material provides for both sides of the fluid apertures to present squarely abutting surfaces when the valved catheter is at rest, and the fluid apertures are in a closed compressed condition. The width of the flexible material layer is selected to be slightly greater than the outside diameter of the distal portion of the elongated tubular member where the flexible material is attached to the outermost portions of the wall. When the valved catheter is at rest, the outermost portions of the wall of the elongated tubular member compress the flexible material layer for forcing the slits o fluid apertures to a closed position, thereby preventing fluid leakage or retrograde blood flow. When the valved catheter is in use, the force of fluid being injected or withdrawn through passages 36 and 37 causes the abutting slit surfaces to laterally stretch, thereby permitting fluid flow through the aperture.

Flexible material layer 43 comprises a material with a desirable durometer and a curing mechanism that is similar to that o the cylindrical silicone tubing material of elongated member 32. Flexible material layer 43 preferably comprises, for example, a silicone material such as Silastic Q7-4850 which is commercially available from Dow Corning, and has a durometer of approximately 50 on the Shore A scale.

Plugs 47 and 48 comprise, for example, the same material as the flexible material layer, which is classified as a liquid silicone and is injected into passages 36 and 37 of the elongated tubular member. The liquid silicone is then heated and cured for closing the distal end of the elongated tubular member.

A preferred method of forming illustrative dual lumen valved catheter 32 is depicted in FIGS. 5–9. FIG. 6 depicts a top view of elongated tubular member 33 positioned in well-known mold half 57 with flat-surface rods 49 and 51 positioned through passages 36 and 37 in distal portion 38, respectively. First rod 49 is a round, metal hard pin such as a gauge pin or drill blank that has been ground down to form flat surface 50 extending longitudinally therealong. Rod 49 also has laterally recessed portions 55 extending from the flat surface and thus forming wide surface segment 59 of the flat surface. Wide surface segment 59 is approximately 0.95" in length extending from the distal end of the first rod. The laterally recessed portion of the rod extends for approximately 0.80" from wide surface segment 59. Laterally recessed portions 55 extend along the length of the rod that is positioned in passage 36 and in proximal segment 54 of distal mold portion 38. Similar to the first rod, second rod 51 has been ground down to form flat surface 52. Second rod 51 also has laterally recessed portions 56 and 60, thereby forming wide surface segment 61. As depicted, laterally recessed portion 56 is positioned in distal segment 53 of distal mold portion 38. Wide surface segment 61, depicted in proximal segment 54 of distal mold portion 38, is approximately 0.30" in length and starts approximately 1.05" from the distal end of the second rod. Laterally recessed portions 56 and 60 extend from wide flat surface segment 61 for approximately 0.70" and 0.40", respectively. As depicted in FIG. 6, the laterally recessed portions of first and second rods 49 and 51 are adjacent wide surface segments 59 and 61 to relieve the stretching of the wall adjacent the laterally recessed portions of the rods. As a result, only the wall of the elongated tubular member adjacent the wide surface segments of the pins is stretched to subsequently compress the fluid aperture to a closed position.

Figure 7:
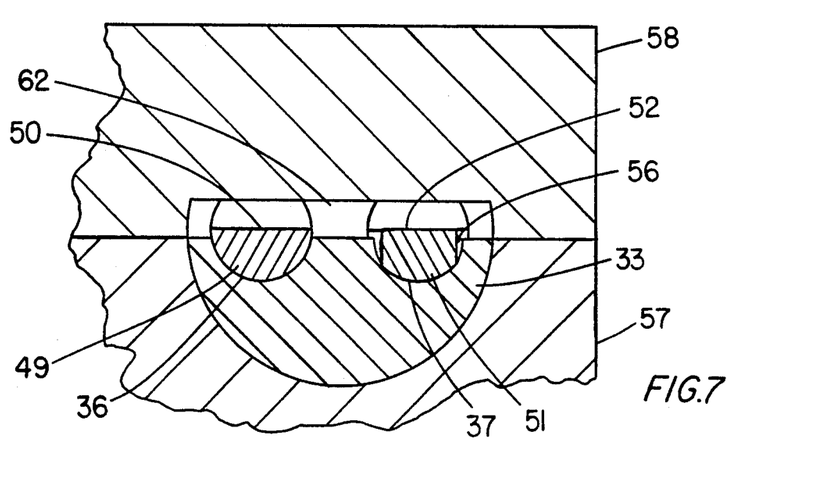

Depicted in FIG. 7 is a cross-sectional view of FIG. 6 along the line 7—7. This cross-sectional view illustrates the positioning of rods 49 and 51 in passages 36 and 37 of the elongated tubular member 33. The top half 58 of the mold is also shown mating with bottom half 57 of the mold, thereby creating a cavity 62 in which flexible material is injected to form flat or planar surface 42 for the valve. Laterally extending portions 56 are shown in second rod 51 extending from flat surrace 52.

Figure 8:
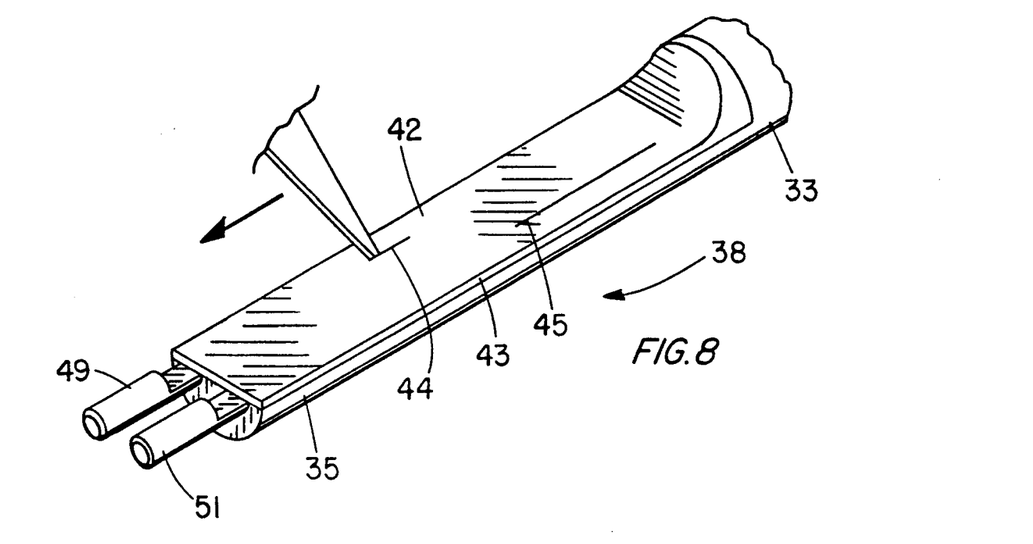

FIG. 8 depicts a pictorial view of elongated tubular member 33 and flexible material layer 43 fixedly attached with rods 49 and 51 positioned in passages 36 and 37, respectively. The catheter has been removed from the mold halves shown in FIGS. 6 and 7. Planar or flat surface 42 of the flexible material is cut longitudinally in the region of the wide surface segments of the respective rods to form longitudinally offset apertures or slits 44 and 45. When the slit is being cut, the rods remain in their respective passages for laterally stretching wall 35 adjacent the wide surface segments of the rods.

Figure 9:
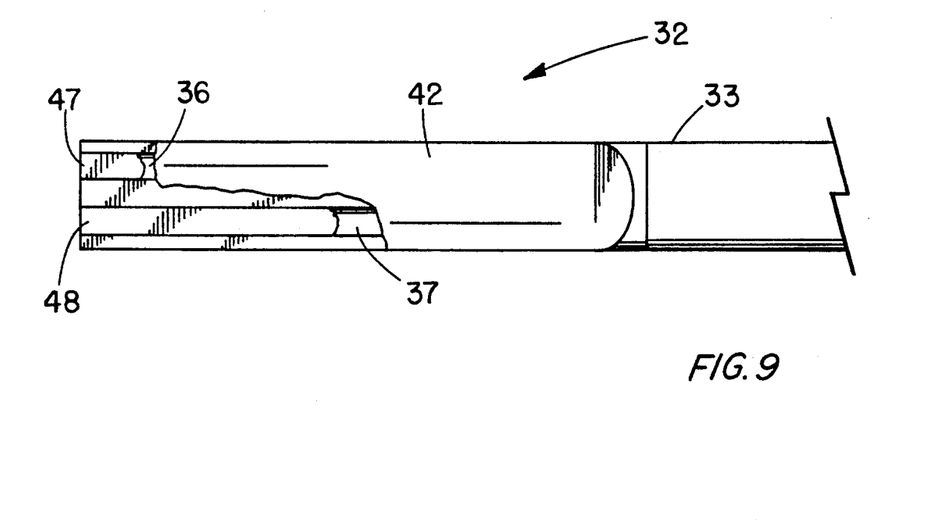

FIG. 9 depicts a partially sectioned top view of the valved catheter with the rods removed from passages 36 and 37. Plugs 47 and 48 are injected as previously described into passages 36 and 37, respectively. The plugs are affixed to the elongated tubular member and flexible tubular layer by injecting material into the distal end of the passages and then heating and curing the material.

It is to be understood that the above-described valved catheter is merely an illustrative embodiment of the principles of this invention and that other valved catheters may be devised by those skilled in the art without departing from the spirit and scope of this invention. It is contemplated that this valve can be utilized on catheters used in other regions of the body besides the vascular system. It is further contemplated that a catheter, particularly a multi-lumen catheter, can include more than one of the above-described valves. It is also further contemplated that the fluid aperture can be oriented in another direction, such as transverse or diagonal with respect to the axis of the elongated member tube. For example, if the fluid aperture is oriented transversely in the above-described illustrative valved catheter, the fluid aperture is biased open when the catheter is at rest and forced closed by fluid flow in the elongated member tube passage. This embodiment of the valved catheter is contemplated for a clinical application wherein a biased open valve is desirable. The opening and closing pressures of the valve can be varied depending on the durometer and thickness of the valve layer material along with varying the dimensions and durometer of the elongated member tube.

What is claimed is:

1. A valved catheter comprising:
   an elongated member having a distal portion, a wall, first and second passages extending longitudinally therein, and a reduced cross section and a planar surface in said distal portion; and
   a valve in said planar surface and having first and second fluid apertures communicating exterior to and with said first and second adjacent passages of said member, respectively.

2. The catheter of claim 1 wherein said planar surface comprises a flat-surfaced layer of flexible material attached to said wall and wherein said first and second fluid apertures comprise first and second slits formed through said flat-surfaced layer of flexible material and communicating exterior to and with said first and second passages of said member, respectively.

3. The catheter of claim 2 wherein an outer surface of said wall along said distal portion has a substantially semi-circular cross-sectional shape and compresses said first and second slits to at least one of a plurality of predetermined positions.

4. The catheter of claim 3 wherein said flat-surfaced layer of flexible material is attached to said wall over said first and second passages.

5. The catheter of claim 2 wherein said first and second slits are positioned longitudinally offset along said first and second passages, respectively.

6. The catheter of claim 1 wherein said member further comprises a closed distal end.

7. The catheter of claim 6 wherein said closed distal end includes first and second plugs positioned in and closing a distal end of said first and second passages of said member, respectively.

8. The catheter of claim 1 wherein said valve is formed by positioning in said first passage along said distal portion a first rod having a flat surface extending longitudinally along said distal portion, a first wide segment of said flat surface of said first rod when in said first passage laterally stretching said wall adjacent thereto.

9. The catheter of claim 8 wherein said valve is formed by positioning in said second passage along said distal portion a second rod having a flat surface extending longitudinally along a second segment of said distal portion, a second wide segment of said flat surface of said second rod when in said second passage laterally stretching said wall adjacent thereto along said second segment of said distal portion.

10. The catheter of claim 9 wherein each of said first and second rods has laterally recessed portions extending from said flat surface thereof adjacent the wide segment of the other rod when said first and second rods are positioned in said first and second passages, respectively.

11. The catheter of claim 10 wherein said valve is further formed by applying a layer of flexible material over said flat surfaces of said first and second rods when in said first and second passages, respectively, and attaching said layer to said wall along said distal portion.

12. The catheter of claim 11 wherein said first aperture is formed by placing a first longitudinal slit in said layer of flexible material along said first wide segment of said flat surface of said first rod when positioned in said first passage.

13. The catheter of claim 12 wherein said second aperture is formed by placing a second longitudinal slit in said layer of flexible material along said second segment of said flat surface of said second rod when positioned in said second passage.

14. The catheter of claim 13 wherein said catheter is further formed by inserting a plug in and closing a distal end of at least one of said first and second passages of said member when said at least one of said first and second rods is removed from said first and second passages, respectively.

15. The catheter of claim 1 wherein said wall stressed about said distal portion compresses at least one of said first and second apertures to a closed position.

16. The catheter of claim 1 wherein said wall about said distal portion compresses said first and second fluid apertures to at least one of a plurality of predetermined positions.

17. A valved catheter comprising:
a flexible material, elongated tubular member having first and second adjacent passages extending longitudinally therein, a wall, a distal portion, and a reduced cross section and a planar surface in said distal portion, said planar surface including a flat-surfaced layer of flexible material attached to said wall over said first and second adjacent passages; and
a valve in said planar surface and having first and second slits formed through said flat-surfaced layer of flexible material and communicating exterior to and with said first and second passages of said member, respectively, said first and second slits being positioned longitudinally offset along said first and second adjacent passages, respectively, an outer surface of said wall along said distal portion having a substantially semi-circular cross-sectional shape and compressing said first and second slits to a closed position; said valve being formed by positioning in said first passage along said distal portion a first rod having a flat surface extending longitudinally along said distal portion, a first wide segment of said flat surface of said first rod when positioned in said first passage laterally stretching said wall adjacent thereto; said valve being formed by also positioning in said second passage along said distal portion a second rod having a flat surface extending longitudinally along said distal portion, a second wide segment of said flat surface of said second rod when positioned in said second passage laterally stretching said wall adjacent thereto, each of said first and second rods having laterally recessed portions extending from said flat surface thereof adjacent the wide segment of the other rod when said first and second rods are positioned in said first and second adjacent passages, respectively; said valve being formed by further applying a layer of flexible material over said flat surfaces of said first and second rods when positioned in said first and second adjacent passages, respectively, and attaching said layer to said wall along said distal portion; said first slit being formed in said layer of flexible material along said first wide segment of said flat surface of said first rod when positioned in said first passage; said second slit being formed in said layer of flexible material along said second wide segment of said flat surface of said second rod when positioned in said second passage; and
first and second plugs positioned in and closing a distal end of said first and second adjacent passages of said member, respectively.

18. A valved catheter (10) comprising an elongated tubular member (11) with a longitudinal passage (14) extending therethrough, a lateral facing valve (12) in the region of the distal end of the catheter, said passageway communicating with said valve
CHARACTERIZED IN THAT
the tubular member in the said region of the distal end is of reduced cross section and has a planar surface (21), and in that a valve (20) is formed in said planar surface.

19. A catheter according to claim 18, wherein the outer wall (13) of the elongated member also forms the said planar surface, and wherein the valve is in the form of a slit (20) extending through the planar surface.

20. A catheter according to claim 18, wherein a longitudinally extending section (18) of the tubular member has been removed in the said region of the distal end, and wherein material (19) has been attached to the member in said region to form the said planar surface.

21. A catheter according to claim 20, wherein the said material is fixed to the member (16, 17) in the said region of the distal end while the latter is in a pre-stressed condition, the pre-stressing serving to ensure that the valve is in a normally closed condition.

22. A catheter according to claim 21, wherein the member in the said region of the distal end is substantially U-shaped, and wherein the said material is flexible, and extends across the ends (16, 17) of the U-shaped distal end.

23. A catheter according to claim 18, wherein a second valve (45) is formed in the said planar surface, and wherein a second longitudinal passage (37) extends through the tubular member and is in sole communication with the second valve.

24. A catheter according to claim 23, wherein a longitudinally extending section of the tubular member has been removed in the said region of the distal end, wherein material has been attached to the member over the first and second passages, and wherein the first and second valves are in the form of first and second slits extending through the planar surface and longitudinally offset along the first and second passages.

25. The catheter according to claim 24, further comprising a plurality of plugs each passage is closed at the distal end thereof by one of said plugs (47, 48).

26. The catheter according to claim 23, wherein said valve is formed by temporarily locating a flat-surfaced rod (49, 51) in each passage during formation of the catheter.

* * * * *